United States Patent
Davis

(10) Patent No.: US 11,569,513 B1
(45) Date of Patent: Jan. 31, 2023

(54) REDOX FLOW BATTERY CARRIER MOLECULE

(71) Applicant: Triad National Security, LLC, Los Alamos, NM (US)

(72) Inventor: Benjamin L. Davis, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 17/335,989

(22) Filed: Jun. 1, 2021

Related U.S. Application Data

(60) Provisional application No. 63/033,560, filed on Jun. 2, 2020.

(51) Int. Cl.
*H01M 8/18* (2006.01)
*H01M 8/02* (2016.01)
*C07F 3/06* (2006.01)

(52) U.S. Cl.
CPC ............... *H01M 8/02* (2013.01); *C07F 3/06* (2013.01); *H01M 8/188* (2013.01); *H01M 2300/0025* (2013.01)

(58) Field of Classification Search
CPC .................................................. H01M 8/02
See application file for complete search history.

(56) References Cited

U.S. PATENT DOCUMENTS

| | | | | |
|---|---|---|---|---|
| 2014/0099569 A1* | 4/2014 | Oh | ............ | H01M 8/20 556/24 |
| 2014/0239906 A1* | 8/2014 | Anderson | ............ | H02J 7/0068 429/105 |

(Continued)

OTHER PUBLICATIONS

Sharma et al., "Iron-iminopyridine complexes as charge carriers for non-aqueous redox flow battery applications," *Energy Storage Materials*, vol. 37, pp. 576-586, Feb. 1, 2021.

*Primary Examiner* — Brian R Ohara
(74) *Attorney, Agent, or Firm* — Klarquist Sparkman, LLP

(57) ABSTRACT

A nonaqueous electrolyte composition for use in a redox flow battery system, comprising:
  a nonaqueous supporting electrolyte; and
  a metal ligand complex of formula II:

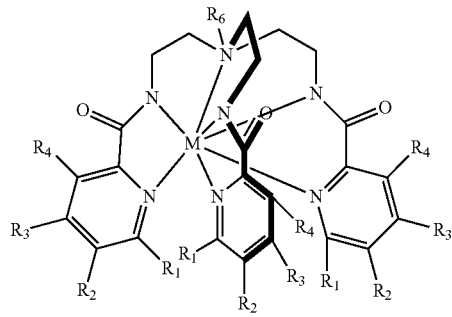

wherein $R_1$, $R_2$, $R_3$, $R_4$ and $R_6$ are each independently H, halogen, alkyl, substituted alkyl, alkoxy, substituted alkoxy, aryloxy, substituted aryloxy, heteroaryloxy, substituted heteroaryloxy, or a polyether, (Continued)

-continued

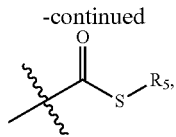

wherein $R_5$ is H, alkyl, or substituted alkyl; and M is a transition metal or zinc.

20 Claims, 10 Drawing Sheets

(56) References Cited

U.S. PATENT DOCUMENTS

| | | | |
|---|---|---|---|
| 2016/0101177 A1* | 4/2016 | Papish | A61K 41/0042 604/20 |
| 2018/0254478 A1* | 9/2018 | Jones | H01M 4/368 |

* cited by examiner

Fully Charged Anolyte/Negolyte

Anolyte/Negolyte

Fe(II)
Ligand: -4 charge
Overall: -2 charge

REDOX FLOW BATTERY CARRIER MOLECULE

CROSS REFERENCE TO RELATED APPLICATION

This application claims the benefit of U.S. Provisional Application No. 63/033,560 filed on Jun. 2, 2020, which is incorporated herein by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

BACKGROUND

Inexpensive grid scale energy storage is required to further utilize renewable energy sources (wind, solar). Although redox flow batteries (RFB) are commercially available, the price is still too high for significant adoption. This price, in part, derives from the poor density of energy storage—which is attributed to the narrow electrochemical window of aqueous media (~1.7 v), poor solubility of the electron carriers (<1 M), and only storing one electron/carrier molecule. The charge carrier described herein will address all three of these shortcomings using a modular design.

SUMMARY

Disclosed herein is a nonaqueous electrolyte composition for use in a redox flow battery system, comprising:
a nonaqueous supporting electrolyte; and
a metal ligand complex of formula II:

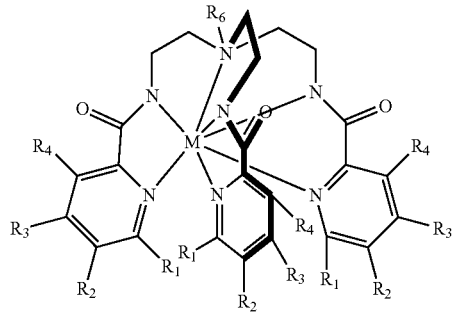

wherein $R_1$, $R_2$, $R_3$, $R_4$ and $R_6$ are each independently H, halogen, alkyl, substituted alkyl, alkoxy, substituted alkoxy, aryloxy, substituted aryloxy, heteroaryloxy, substituted heteroaryloxy, or a polyether,

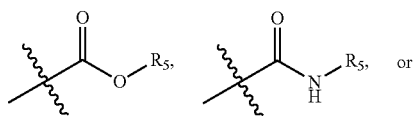

-continued

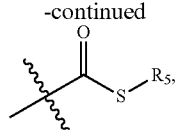

wherein $R_5$ is H, alkyl, or substituted alkyl; and M is a transition metal or zinc.

Also disclosed herein is a ligand metal complex of formula II:

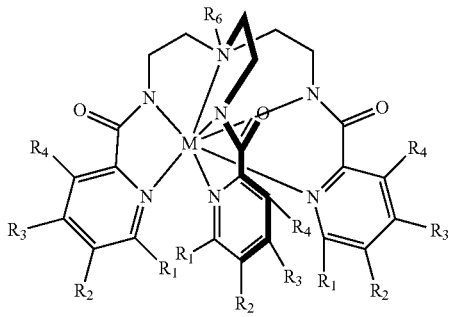

wherein $R_1$, $R_2$, $R_3$, $R_4$ and $R_6$ are each independently H, halogen, alkyl, substituted alkyl, alkoxy, substituted alkoxy, aryloxy, substituted aryloxy, heteroaryloxy, substituted heteroaryloxy, or a polyether,

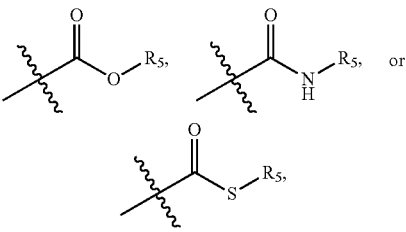

wherein $R_5$ is H, alkyl, or substituted alkyl; and M is a transition metal or zinc.

The foregoing will become more apparent from the following detailed description, which proceeds with reference to the accompanying figures.

DETAILED DESCRIPTION

Terminology

Figure 1:
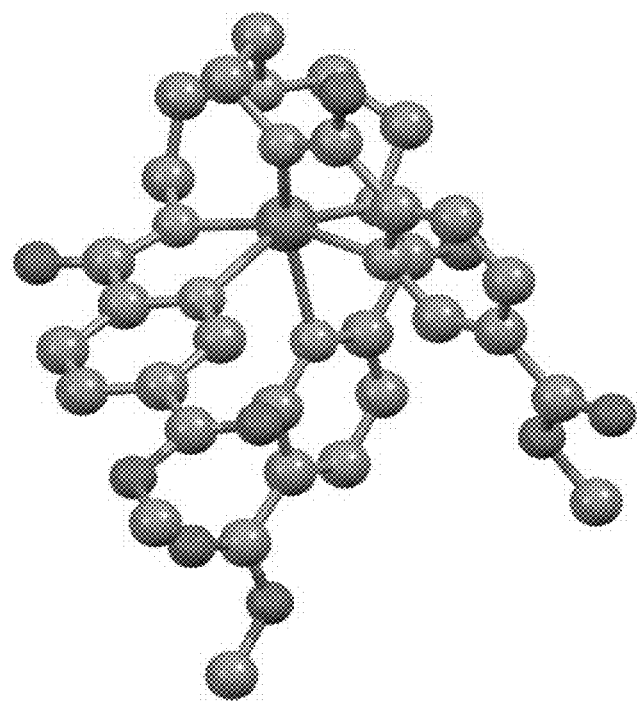
FIG. 1. Solid state structure of Fe III tris(2-aminoethyl) amine (TREN) picolinic (PIC) (referred to as "Fe(TREN-PIC)") complex.
Figure 2:
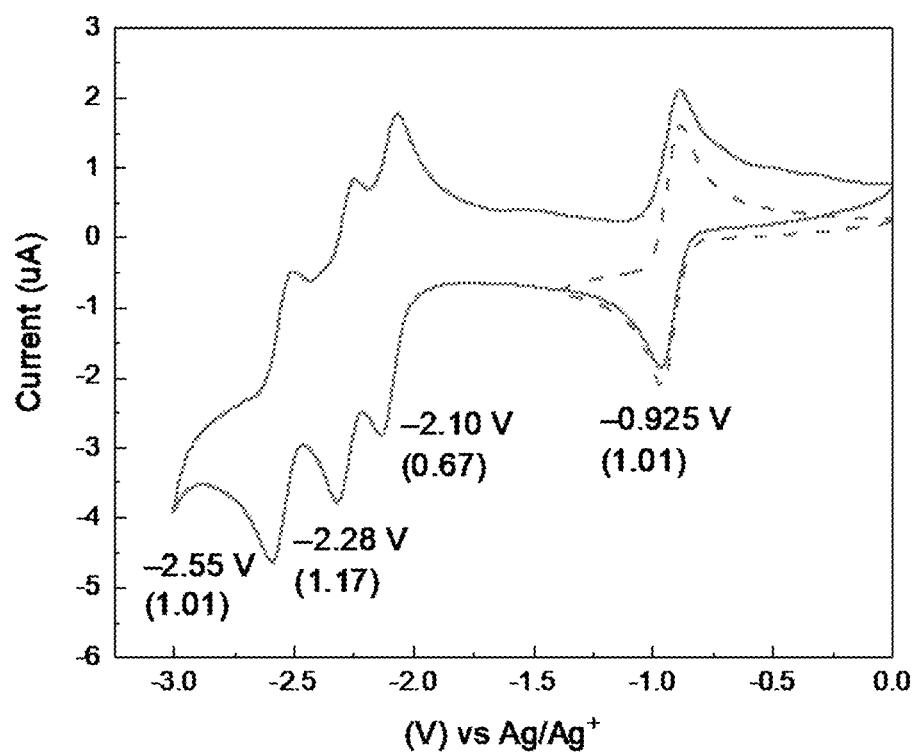
FIG. 2. Voltammogram of the anodic/negative region of a 1 mM solution of Fe(TREN-Pic) in 0.1 M tetrabutylammonium hexafluorophosphate (TBAPF6) in acetonitrile (MeCN), obtained using a glassy carbon working electrode, a platinum wire counter electrode, and a 0.010 M $AgBF_4$ reference electrode.
Figure 3:
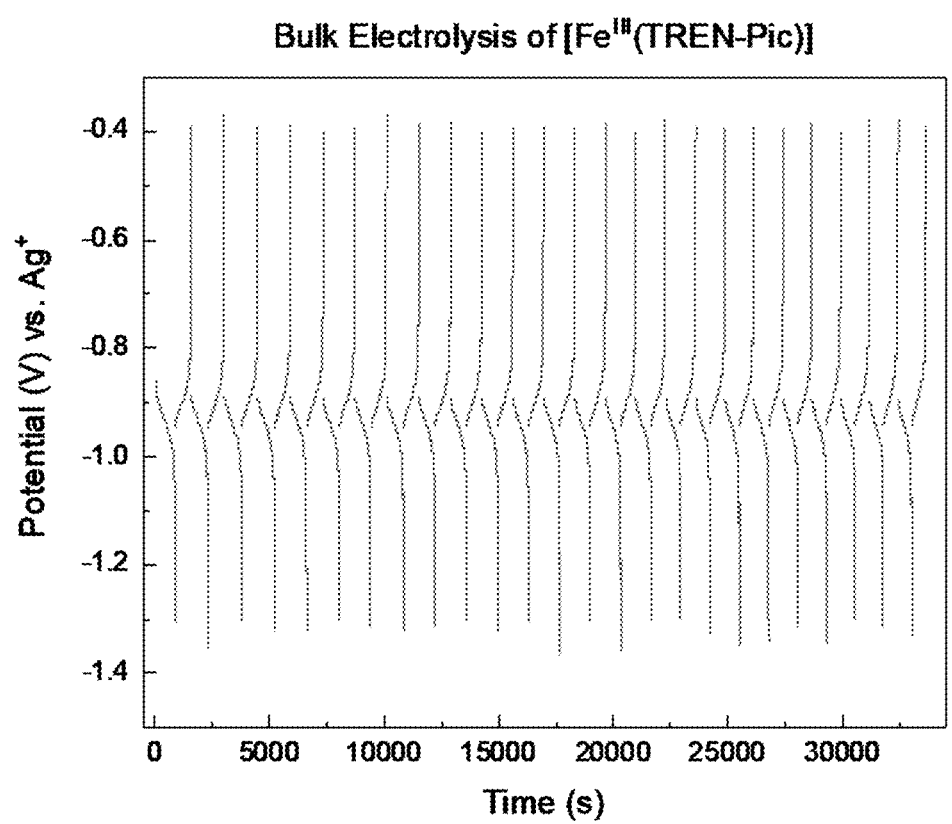
FIG. 3. Galvanostatic 1 electron charging and discharging of a 1 mM solution of Fe(TREN-Pic) in 0.1 M TBAPF6 in MeCN, charging and discharging rates were both 1 mA and potential cutoffs were −1.3 V vs $Ag^+$ during charging and −0.4 V vs $Ag^+$ during discharging.
Figure 4:
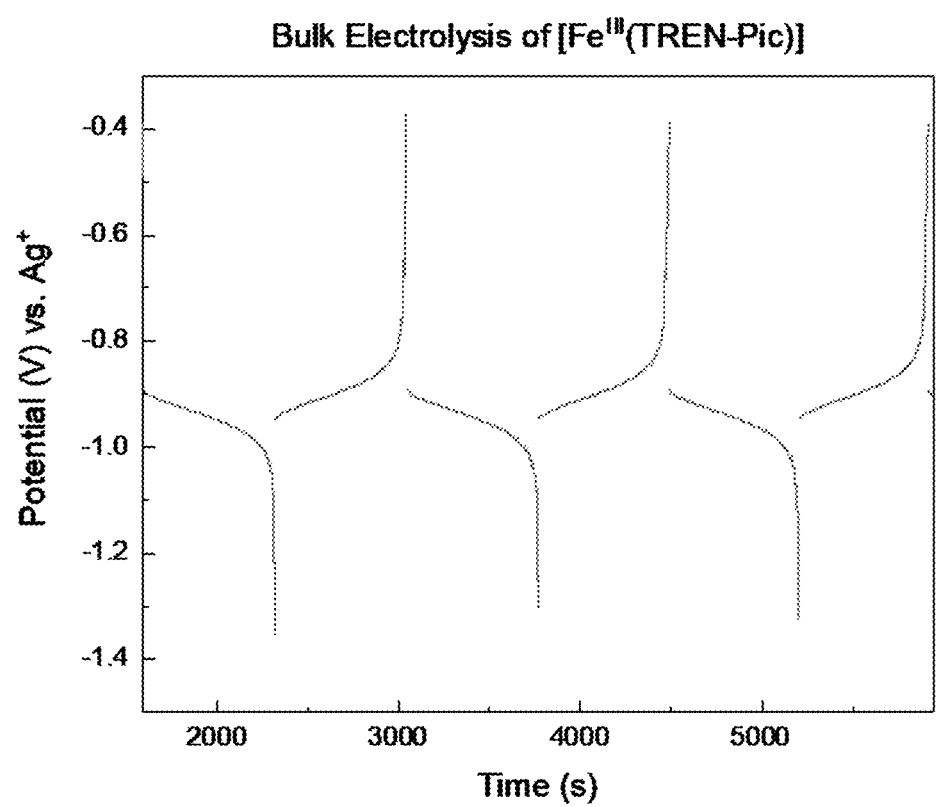
FIG. 4. Close-up of FIG. 3.
Figure 5:
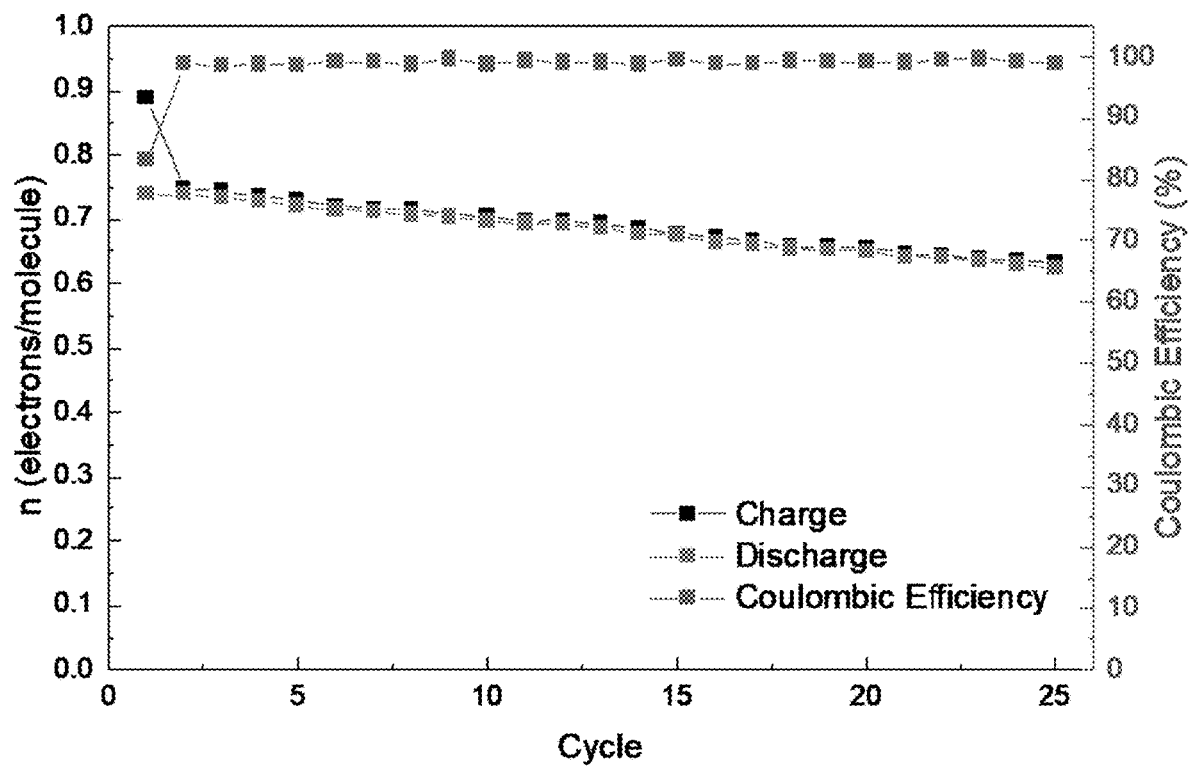
FIG. 5. Metrics obtained from bulk electrolysis displaying high coulombic efficiencies for the charge/discharge cycling.
Figure 6:
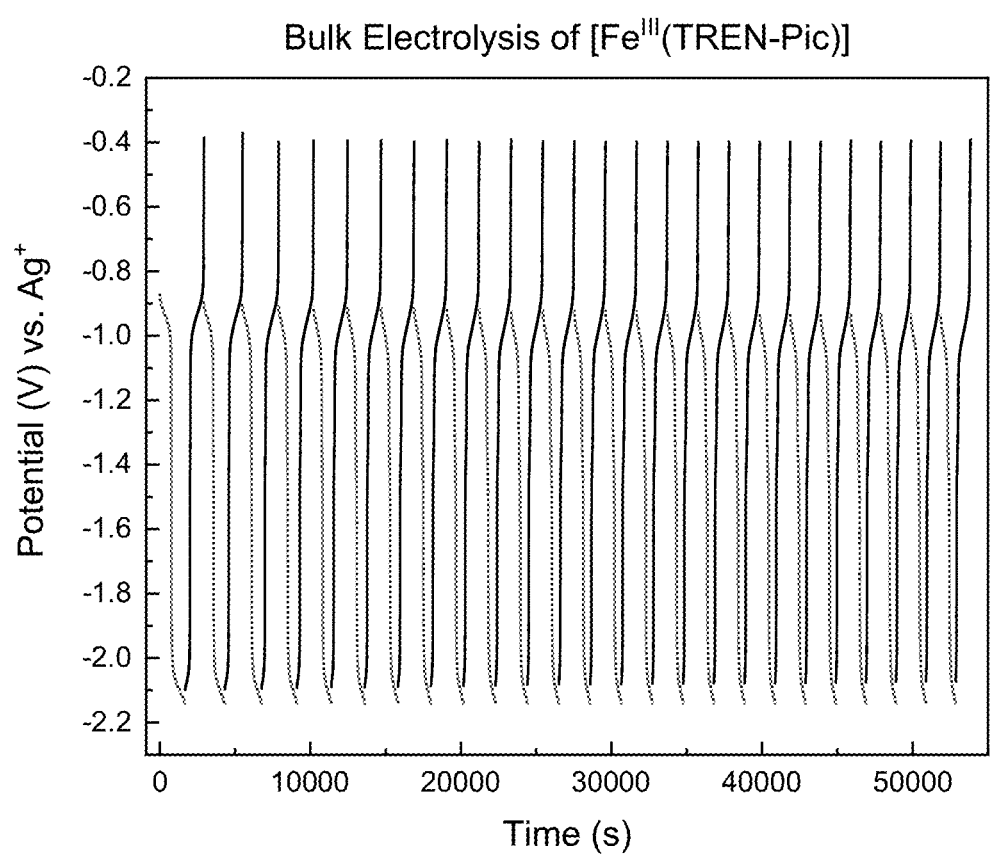
FIG. 6. Galvanostatic 2 electron charging and discharging of a 1 mM solution of Fe(TREN-Pic) in 0.1 M TBAPF6 in MeCN, charging and discharging rates were both 1 mA and potential cutoffs were −2.14 V vs Ag$^+$ during charging and −0.4 V vs Ag$^+$ during discharging.
Figure 7:
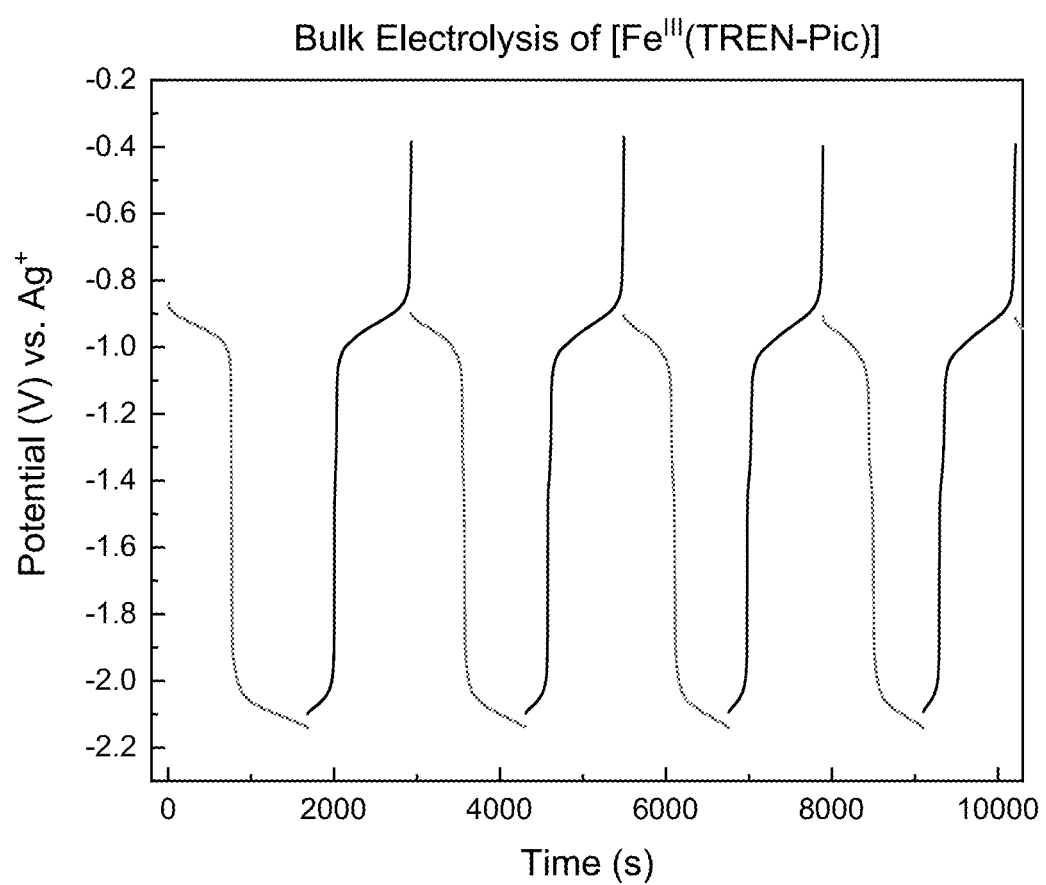
FIG. 7. Close-up of FIG. 6.
Figure 8:
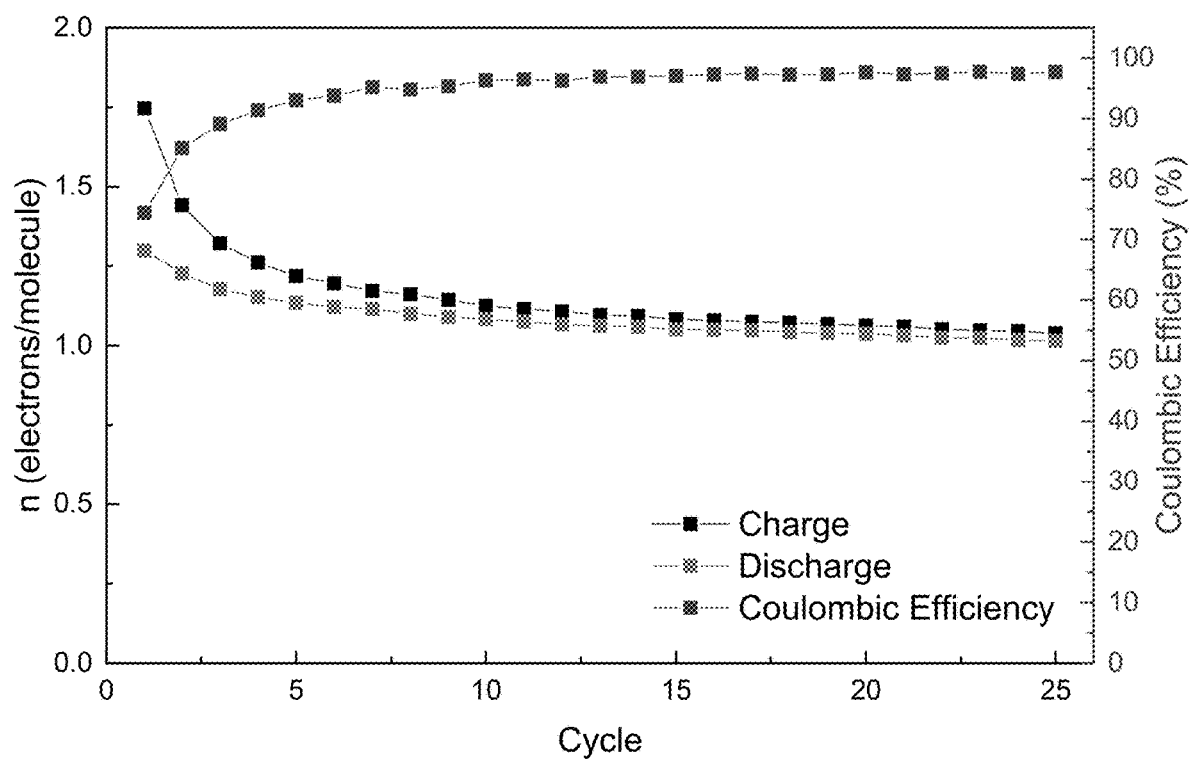
FIG. 8. Metrics obtained from bulk electrolysis displaying high coulombic efficiencies for the charge/discharge cycling and the complexes capability to reversibly store multiple electron equivalents.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl.

"Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

"Aryloxy" or "heteroaryloxy" refers to a group of the formula —OAr, wherein Ar is an aryl group or a heteroaryl group, respectively.

Capacity: The capacity of a battery is the amount of electrical charge a battery can store (charge capacity) and deliver (discharge capacity). The discharge capacity is typically expressed in units of mAh, or Ah, and indicates the maximum charge a battery can produce over a period of one hour. The term "capacity fade" refers to a decrease in the charge capacity over time and result in shorter charge/discharge cycles when the current/voltage is held constant. The term "carboxylate" or "carboxyl" refers to the group —COO$^−$ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

Cell: As used herein, a cell refers to an electrochemical device used for generating a voltage or current from a chemical reaction, or the reverse in which a chemical reaction is induced by a current. Examples include voltaic cells, electrolytic cells, redox flow cells, and fuel cells, among others. Multiple single cells can form a cell assembly, often termed a stack. A battery includes one or more cells, or even one or more stacks.

Coulombic efficiency (CE): The efficiency with which charges are transferred in a system facilitating an electrochemical reaction. CE may be defined as the amount of charge exiting the battery during the discharge cycle divided by the amount of charge entering the battery during the charging cycle.

Electrochemically active component: A component (an element, an ion, or a compound) that is capable of forming redox pairs having different oxidation and reduction states, e.g., ionic species with differing oxidation states or a metal cation and its corresponding neutral metal atom. In a flow battery, an electrochemically active component refers to the chemical species that participate in the redox reaction during the charge and discharge processes, significantly contributing to the energy conversions that ultimately enable the battery to deliver/store energy. By "significantly contributing" is meant that a redox pair including the electrochemically active component contributes at least 10% of the energy conversions that ultimately enable the battery to deliver/store energy. In some embodiments, the redox pair including the electrochemically active component contributes at least 50%, at least 75%, at least 90%, or at least 95% of the energy conversions in a catholyte or anolyte comprising the electrochemically active component.

Electrolyte: A substance containing free ions and/or radicals that behaves as an ionically conductive medium. In a redox flow battery, some of the free ions and/or radicals are electrochemically active components. An electrolyte in contact with the anode, or negative half-cell, may be referred to as an anolyte, and an electrolyte in contact with the cathode, or positive half-cell, may be referred to as a catholyte. The anolyte and catholyte are often referred to as the negative electrolyte and positive electrolyte, respectively, and these terms can be used interchangeably. As used herein, the terms anolyte and catholyte refer to electrolytes composed of electrochemically active components and a nonaqueous supporting solution.

Energy efficiency (EE): The product of coulombic efficiency and voltage efficiency. EE=CE×VE.

Half-cell: An electrochemical cell includes two half-cells. Each half-cell comprises an electrode and an electrolyte. A redox flow battery has a positive half-cell in which electrochemically active components are oxidized, and a negative half-cell in which electrochemically active components are reduced during charge. Opposite reactions happen during discharge.

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$ cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

Voltage efficiency (VE): The voltage produced by the battery while discharging divided by the charging voltage.

Working potential: The electrode potential of a cell constructed with a standard hydrogen electrode and the electrode/redox pair under investigation.

Particular examples of the presently disclosed compounds may include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The presently disclosed compounds can have at least one asymmetric center or geometric center, cis-trans center (C═C, C═N). All chiral, diasteromeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}F$, etc Ligand Metal Complexes Disclosed herein are ligand metal complexes for inclusion in an electrolyte composition for a non-aqueous redox flow battery (RFB). In particular, the ligand metal complexes can be employed as an electrically active component (e.g., a redox active charge storage material). In certain embodiments, the ligand metal complex that can function as a multi-electron storage vessel in the anodic (negolytic) compartment of a redox flow battery.

The complex is formed by complexing a metal (e.g., the element iron (Fe)) with three anionic picolinic amides connected together with a tris(2-aminoethyl)amine (TREN) moiety. The ligand provides multidendate coordination for robust coordination complexes, amide groups that function as electron reservoirs, and low molecular weight for high intrinsic capacity.

In certain embodiments, the resulting redox carrier has the ability to store two electrons per molecule at −0.93 and −2.1V (vs. Ag+/Ag reference) and has a modular design to address issues of solubility and reversibility.

In certain embodiments, the ligand has a structure of formula I:

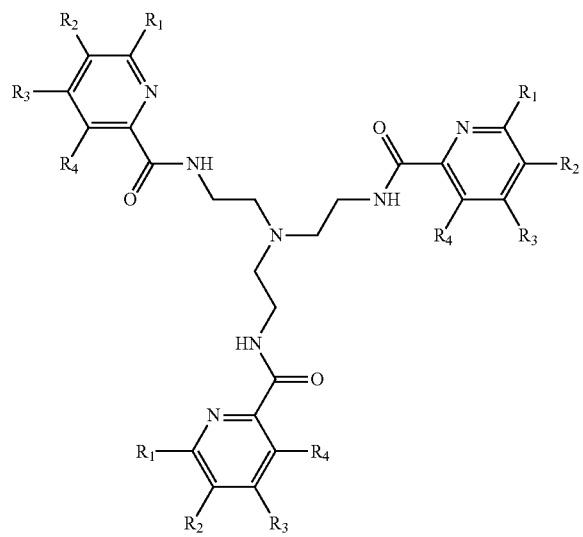

wherein $R_1$, $R_2$, $R_3$ and $R_4$ are each independently H, halogen, alkyl, substituted alkyl, alkoxy, substituted alkoxy, aryloxy, substituted aryloxy, heteroaryloxy, substituted heteroaryloxy, or a polyether.

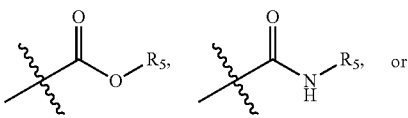

-continued

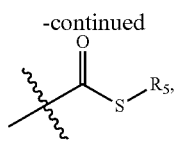

wherein $R_5$ is H, alkyl, or substituted alkyl. In certain embodiments, the ligand metal complex has a structure of formula II:

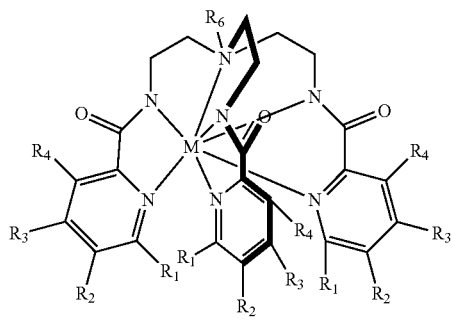

wherein $R_1$, $R_2$, $R_3$, $R_4$ and $R_6$ are each independently H, halogen, alkyl, substituted alkyl, alkoxy, substituted alkoxy, aryloxy, substituted aryloxy, heteroaryloxy, substituted heteroaryloxy, or a polyether.

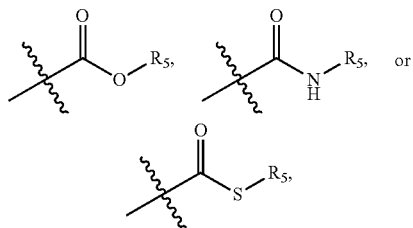

wherein $R_5$ is H, alkyl, or substituted alkyl; and M is a transition metal or zinc.

In certain embodiments, each $R_2$ is

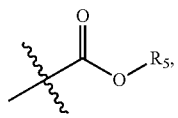

particularly wherein $R_5$ is alkyl, such as $C_1$-$C_6$ alkyl. In certain embodiments, $R_5$ is methyl.

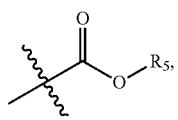

In certain embodiments, each of $R_1$, $R_3$, $R_4$ and $R_6$ is H, and $R_2$ is particularly wherein $R_5$ is alkyl, such as $C_1$-$C_6$ alkyl. In certain embodiments, $R_5$ is methyl.

In certain embodiments, each of $R_1$, $R_2$, $R_3$, $R_4$ and $R_6$ is H.

In certain embodiments, M is scandium, titanium, vanadium, chromium, manganese, iron, cobalt, nickel, copper, or zinc. In certain embodiments, M is nickel, iron, cobalt, chromium or zinc. In certain embodiments, M is nickel. In certain embodiments, M is iron.

Redox Flow Battery System

Figure 9:
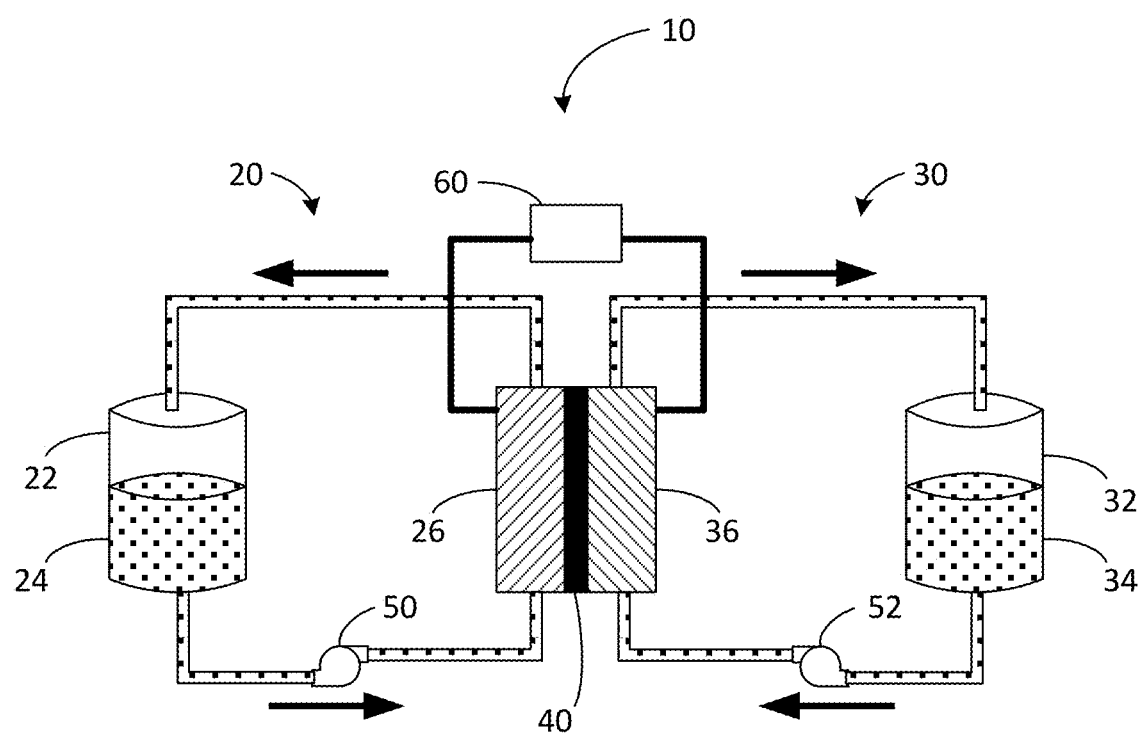
FIG. 9 is a schematic diagram of an exemplary redox flow battery system.
Figure 10:
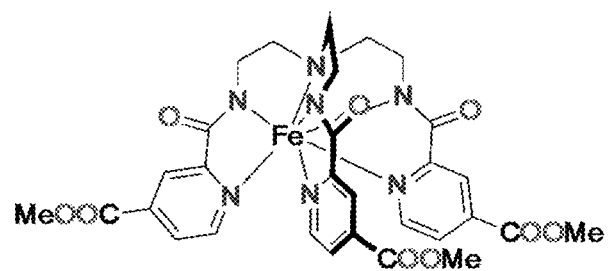
FIG. 10 depicts a fully charged anolyte/negolyte species.

Redox flow batteries (RFBs) can provide electrical energy converted from chemical energy continuously, and are promising systems for energy storage to integrate renewable energies (e.g., solar and/or wind energy) into electrical supply grids. As shown in FIG. 9, a typical RFB system 10 comprises a positive half-cell 20 and a negative half-cell 30. The half-cells are separated by a membrane or separator 40, such as an ion-exchange membrane (cation- or anion-exchange membrane), ion conductive membrane (polymer or ceramic) or porous separator. The positive half-cell 20 comprises an electrode tank 22 containing a catholyte 24 and the negative half-cell 30 comprises an electrode tank 32 containing an anolyte 34. The anolyte and catholyte are solutions comprising electrochemically active components in different oxidation states. The electrochemically active components in the catholyte and anolyte couple as redox pairs. In some embodiments, at least one of the catholyte and anolyte redox active materials remains fully soluble during the charging and discharging cycles of the RFB. However, one member of a redox pair may be insoluble or partially soluble during the charging and discharging cycles of the RFB. For example, when the anolyte comprises a metal cation/metal atom redox pair, only the cation can remain fully soluble during the charging and discharging cycles.

During charging and discharging of the RFB, the catholyte and anolyte are continuously circulating via pumps 50, 52 through the positive and negative electrodes 26, 36, respectively, where redox reactions proceed, providing the conversion between chemical energy and electrical energy or vice-versa. To complete the circuit during use, positive and negative electrodes (including a current collector at each side) 26, 36 of the RFB system 10 are electrically connected through current collectors (not shown) with an external load 60. Redox flow battery systems include an anode and a cathode. Suitable electrodes include carbon-based electrodes and metal-based electrodes. Suitable metal-based electrodes include, but are not limited to, gold, Pt-coated gold, or Pt-coated carbon-based material. Various catalyst particles, such as Pt and Au, can be deposited on the electrode surface to improve the flow battery performance Carbon-based materials with different forms and/or structures can also be used, such as porous carbon (e.g., carbon felt, graphite felt), carbon nanotubes, nanowires, and graphene.

The separator can be a polymer, a ceramic, an ion exchange membrane or an ion permeable membrane. Examples of porous separators include Celgard® polypropylene or polyethylene separators, Tonen® separators, Daramic® polyethylene/silica separators, Amer-Sil® polyvinyl chloride/silica separators, polytetrafluoroethylene/silica separators, and TAMED ceramic filter membranes. Examples of porous membranes include sulfonated fluoropolymers and copolymers, sulfonated polyolefin polymers, and sulfonated aromatic-containing polymers.

In charging, the electrical energy supplied causes a chemical reduction reaction in one electrolyte and an oxidation reaction in the other. The separator between the cathode portion and the anode portion inhibits the electrolytes from mixing but allow selected ions to pass through to complete the oxidation/reduction (redox) reaction. On discharge, the chemical energy contained in the electrolyte is released in the reverse reaction and electrical energy can be drawn from the electrodes.

The ligand metal complex is present in the electrolyte-containing composition, either with or without a separate solvent. The electrolyte-containing composition may also include at least one supporting electrolyte. In certain embodiments, the ligand metal complex (or species thereof) is present in the electrotype composition in an amount of at least 1 M in all charge states. In certain embodiments, the ligand metal complex (or species thereof) is present in the electrotype composition in an amount of at least 5 mM, preferably in an amount of at least 10 mM, and more preferably in an amount of at least 15 mM, in all charge states. In certain embodiments, the supporting electrolyte is present in the electrolyte-containing composition in an amount of 0.1-0.5 M.

Examples of a non-aqueous solvent include a chain-type carbonate (such as diethyl carbonate, dimethyl carbonate, and dipropyl carbonate), acetonitrile, γ-butyrolactone ("GBL"), a cyclic carbonate (such as propylene carbonate ("PC"), ethylene carbonate ("EC"), and butylene carbonate), N-methyl-2-pyrrolidone ("NMP"), fluoroethylene carbonate, N,N-dimethylformamide ("DMF"), N,N-dimethylacetamide ("DMA"), dimethylsulfoxide ("DMSO"), dichloromethane, chloroform, benzene, toluene, xylene, chlorobenzene, methyl acetate, ethyl acetate, acetone, methyl ethyl ketone, cyclohexanone, diethyl ether, 1,2-dimethoxyethane, 1,2-diethoxyethane, tetrahydrofuran, 1,4-dioxane, methanol, ethanol, and a mixture thereof.

Examples of a supporting electrolyte include $LiBF_4$, $LiPF_6$, $LiSbF_6$, $LiAsF_6$, $LiClO_4$, $LiCF_3SO_3$, $Li(CF_3SO_2)_2N$, $LiC_4F_9SO_3$, $LiAlO_2$, $LiAlCl_4$, $LiN(C_xF_{2x+1}SO_2)(C_yF_{2y+1}SO_2)$ (wherein x and y are natural numbers), $NaBF_4$, $NaPF_6$, $Na_2SO_4$, tetraethylammonium tetrafluoroborate, tetrabutylammonium tetrafluoroborate, tetrabutylammonium hexafluorophosphate, trimethylsulfonylchloride, and a mixture thereof.

Examples

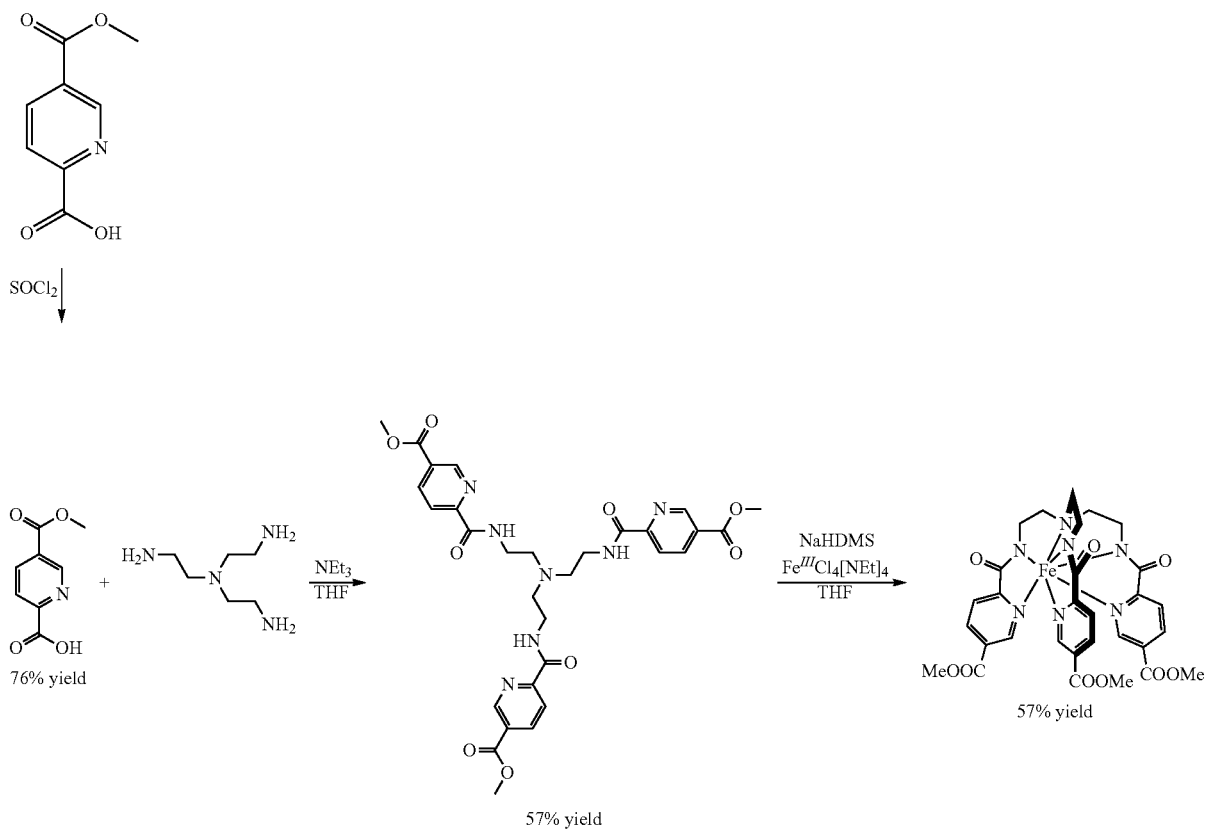

Scheme 1 Synthetic pathway to Fe(TREN-Pic)

Synthesis and Characterization:
Synthesis of TREN-Picolinamide Pro-ligand:

The TREN-picolinamide pro-ligand was prepared based on the literature (Dalton Trans. 2014, 43, 11579). 0.513 g (2.173 mmol) of 1 were dissolved in 20 mL of THF in a 100 mL RBF in an argon glovebox. 0.605 mL (4.344 mmol) of triethyl amine (TEA) were added to the RBF, forming a cream-colored cloudy solution. 0.108 mL (0.724 mmol) were diluted in 3 mL of THF and added dropwise to the solution with stirring. The yellow suspension stirred for 24 h. Next, the product was extracted using 10 mL saturated aqueous NH4Cl and (3×30 mL DCM). The organic layers were combined, washed with brine, and dried over sodium sulfate. The solvent was removed under reduced pressure and the material was purified using column chromatography on silica gel in a solvent solution of 10% methanol in DCM. A $^1$HNMR was taken of the product in chloroform-d. (0.2644 g, 57.45% yield). $^1$H NMR (500M Hz, Chloroform-d) δ 8.80 (s, 3H), 8.61 (s, 3H), 8.34 (d, J=8.0 Hz, 3H), 8.13 (d, J=8.0 Hz, 3H), 3.96 (s, 9H), 3.50 (s, 6H), 2.86 (s, 6H)

Synthesis of Fe (III) TREN-Pic Complex:

In a glovebox, 0.0908 g (0.143 mmol) of the proligand was weighed and added to a reaction vessel along with 0.0786 (0.4286 mmol) of NaHDMS. 10 mL of THF was added, forming a cloudy white suspension. Separately, 0.0469 g (0.143 mmol) Fe(III)Cl4[NEt4] was dissolved in 10 mL THF and added dropwise to the ligand solution. The reaction was allowed to stir for 24 h. Next, the vessel was removed from the glovebox and the solvent was removed. The orange solid was triturated with ether and filtered. The isolated solid was purified on a silica gel column with an initial solution of 5% methanol in DCM and then 10% methanol in DCM. A $^1$HNMR was taken in chloroform-d, but was inconclusive. A crystal structure of the complex was obtained from vapor diffusion pentane into a saturated $CHCl_3$ solution. (0.0562 g, 57.1% yield).

The electrochemical features of the Fe (III) TREN-Pic complex were evaluated. The results are shown in FIGS. 1-8 and described below.

In the negative portion of a cyclic voltammogram four features at −0.93, −2.10, −2.28, and −2.55V are observed with current ratios (i[cathodic]/i[anodic]) of 1.01, 0.67, 1.17, and 1.01 respectively. These were obtained with a 1 mM solution of Fe(TREN-Pic) in 0.1M tetrabutylammonium hexafluorophosphate in acetonitrile using a glassy carbon working electrode, platinum wire counter, and a 0.01M silver tetrafluoroborate reference electrode. When the −0.93V wave is subjected to bulk electrolytic cycling over 25 repetitions, a high Coulombic efficiency is calculated (~95%) with an unoptimized slow decay in utilization (electrons stored per redox carrier molecule) of 4% over the first ten cycles. More impressively, when the voltage window is broadened to include the next wave (−2.28V), bulk cycling indicated successful utilization of this wave although significant decay was observed over 25 cycles. This represents only the third known complex to display this behavior (JACS, 2016, 15378 and Journal of Power Sources, 2016, 681).

In view of the many possible embodiments to which the principles of the disclosed invention may be applied, it should be recognized that the illustrated embodiments are only preferred examples of the invention and should not be taken as limiting the scope of the invention.

What is claimed is:

1. A nonaqueous electrolyte composition for use in a redox flow battery system, comprising:
   a nonaqueous supporting electrolyte; and
   a metal ligand complex of formula II:

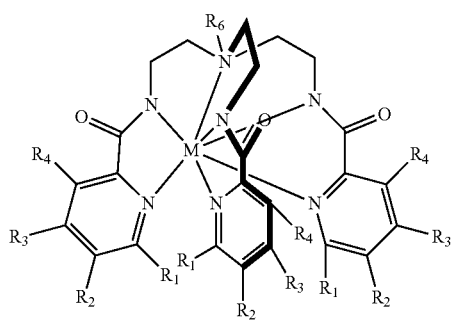

wherein $R_1$, $R_2$, $R_3$, $R_4$ and $R_6$ are each independently H, halogen, alkyl, substituted alkyl, alkoxy, substituted alkoxy, aryloxy, substituted aryloxy, heteroaryloxy, substituted heteroaryloxy, or a polyether,

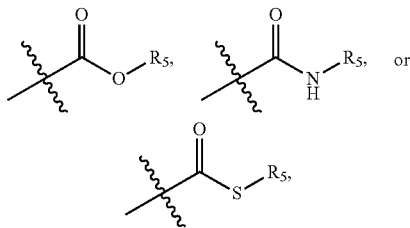

wherein $R_5$ is H, alkyl, or substituted alkyl; and M is a transition metal or zinc.

2. The composition of claim 1, wherein each $R_2$ is

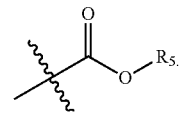

3. The composition of claim 2, wherein $R_5$ is alkyl.

4. The composition of claim 2, wherein $R_5$ is $C_1$-$C_6$ alkyl.

5. The composition of claim 2, wherein $R_5$ is methyl.

6. The composition of claim 2, wherein $R_1$, $R_3$, $R_4$ and $R_6$ is H.

7. The composition of claim 1, wherein M is iron.

8. The composition of claim 2, wherein M is iron.

9. The composition of claim 1, wherein the metal ligand complex of formula II is present in the electrotype composition in an amount of at least 1 M in all charge states.

10. The composition of claim 1, further comprising a non-aqueous solvent.

11. A redox flow battery system, comprising:
    the nonaqueous electrolyte composition of claim 1; and
    an ion-exchange membrane or porous separator.

12. A ligand metal complex of formula II:

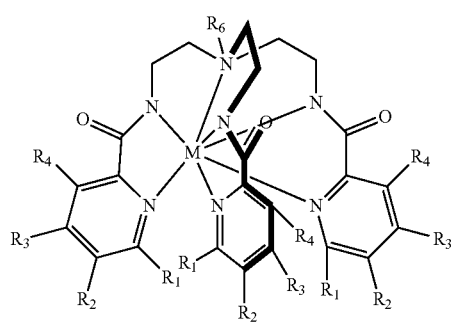

wherein $R_1$, $R_2$, $R_3$, $R_4$ and $R_6$ are each independently H, halogen, alkyl, substituted alkyl, alkoxy, substituted alkoxy, aryloxy, substituted aryloxy, heteroaryloxy, substituted heteroaryloxy, or a polyether,

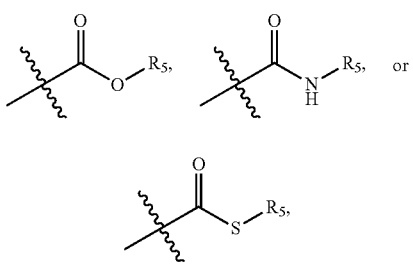

wherein $R_5$ is H, alkyl, or substituted alkyl; and M is a transition metal or zinc.

13. The complex of claim 12, wherein each $R_2$ is

14. The complex of claim 13, wherein $R_5$ is alkyl.
15. The complex of claim 13, wherein $R_5$ is $C_1$-$C_6$ alkyl.
16. The complex of claim 13, wherein $R_5$ is methyl.
17. The complex of claim 12, wherein $R_1$, $R_3$, $R_4$ and $R_6$ is H.
18. The complex of claim 12, wherein M is iron.
19. The complex of claim 12, wherein M is iron.
20. The system of claim 11, each $R_2$ is

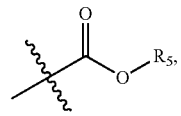

$R_5$ is $C_1$-$C_6$ alkyl, and M is iron.

* * * * *